United States Patent
Kawakami et al.

[11] Patent Number: 5,416,204
[45] Date of Patent: May 16, 1995

[54] METHOD FOR PREPARING 2'-3'-DIDEOXY-β-NUCLEOSIDES USING 2,2-DIDEOXY-DI(ORGANOTHIO)-PENTOFURANOSE INTERMEDIATES

[75] Inventors: Hiroshi Kawakami; Katsuya Matsumoto; Koshi Koseki; Takashi Ebata; Hajime Matsushita, all of Yokohama; Kazuo Itoh; Yoshitake Naoi, both of Tokyo, all of Japan

[73] Assignee: Japan Tobacco, Incorporated, Tokyo, Japan

[21] Appl. No.: 971,768

[22] PCT Filed: Jun. 12, 1992

[86] PCT No.: PCT/JP92/00752
§ 371 Date: Feb. 12, 1993
§ 102(e) Date: Feb. 12, 1993

[87] PCT Pub. No.: WO92/22548
PCT Pub. Date: Dec. 23, 1992

[30] Foreign Application Priority Data
Jun. 14, 1991 [JP] Japan .................. 3-143446

[51] Int. Cl.$^6$ .............. C07H 19/073; C07H 1/00
[52] U.S. Cl. ................... 536/28.2; 536/28.5; 536/28.51; 536/28.52; 536/28.53; 536/28.54; 536/28.55
[58] Field of Search ............ 536/28.2, 28.5, 28.51, 536/28.52, 28.53, 28.54, 28.55, 55.3

[56] References Cited
U.S. PATENT DOCUMENTS

| | | | |
|---|---|---|---|
| 4,921,950 | 5/1990 | Wilson | 536/28.54 |
| 4,987,224 | 1/1991 | Chu | 536/28.2 |
| 5,101,023 | 3/1992 | Czernecki et al. | 536/28.54 |
| 5,220,003 | 6/1993 | Jung et al. | 536/28.2 |

OTHER PUBLICATIONS
Kawakami et al., Chemical Abstracts, vol. 117, 1992, p. 728, col. 2, abstract No. 251686g.

Primary Examiner—John W. Rollins
Assistant Examiner—Gary L. Kunz
Attorney, Agent, or Firm—Birch, Stewart, Kolasch, Birch

[57] ABSTRACT

2,3-Dideoxy-2,2-di(organothio)-B-D-pentofuranosyl-pyrimidines are disclosed as intermediates in the synthesis of 2', 3'-dideoxynucleosides and have the structure shown below.

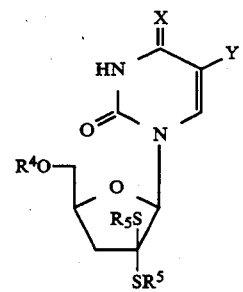

wherein
R$^4$ is a hydroxyl protecting group;
X is oxygen or nitrogen, said nitrogen being bonded to a hydrogen atom, an alkyl or acyl group;
Y is hydrogen, halogen, alkyl, haloalkyl or haloalkenyl; and
R$^5$ is alkyl, aralkyl, or aryl wherein aralkkyl or aryl is substituted with hydrogen, halogen, nitro or alkoxy.

2', 3'-Dideoxynucleosides, products of the above intermediates, are useful as antiviral agents.

4 Claims, No Drawings

METHOD FOR PREPARING 2'-3'-DIDEOXY-β-NUCLEOSIDES USING 2,2-DIDEOXY-DI(ORGANOTHIO)-PENTOFURANOSE INTERMEDIATES

TECHNICAL FIELD

The present invention relates to a method of manufacturing 2',3'-dideoxy-β-nucleoside. 2',3'-dideoxy-β-nucleoside itself is a compound having an antiviral activity. For example, the compound exhibits anti-AIDS virus activity. Further, the compound can be used as a raw material for manufacturing the other compounds which are associated with the compound of the present invention, and are useful as medicines.

BACKGROUND ART

The conventional methods of manufacturing 2',3'-dideoxy-β-nucleoside include, for example,
 a method in which the hydroxyl groups in the 2'-and 3'-positions are selectively removed from (i) ribonucleoside derivatives or (ii) 2'-deoxynucleoside derivatives, and
 (iii) a method utilizing a condensation reaction between a 2,3-dideoxyribose derivative and a base which is a composition of a nucleoside.

An example of conventional method (i) is described in, for example, "J. Org. Chem., 1988, vol. 53, page 5170". It is described that 2',3'-cyclic ortho ester of uridine is thermally decomposed to obtain 2',3',-dideoxy-β-uridine. Then, the base of the nuclooside thus obtained is replaced by another base by using a special strain of *Escherichia coli*.

An example of conventional method (ii) is described in, for example, "Synth. Commun., 1985, vol. 15, page 401". It is described that the hydroxyl group in the 3'-position of 2'-deoxynucleoside is converted into a thiocarbonate ester, followed by subjecting the resultant compound to a deoxidation reaction.

Further, conventional method (iii) is exemplified in, for example, Japanese Patent Application No. 2-6970 filed by the present inventors, "Heterocycles, 1990, vol. 31, page 2041", "Tetrahedron Lett., 1988, vol. 29, page 1239, Falina et al" and "J. Org. Chem., 1988, vol. 53, page 4780, Okabe et al".

In conventional method (i), however, it is necessary to use a bacterium which is difficult to obtain in general. Also, in each of conventional methods (i) and (ii), ribonucleoside derivatives available in the nature are used as raw materials. Thus, in the case of manufacturing various derivatives, it is necessary to prepare a synthetic riboculeoside, followed by converting the synthetic riboculeoside into the desired 2',3'-dideoxy-β-nucleoside derivative.

On the other hand, the conventional method (iii) is poor in its stereoselectivity. Specifically, the product obtained by the conventional method (iii) is a mixture of a desired β-isomer and a α-isomer as byproduct. The mixing ratio of β:α is 7:3 even in the highest case. In general, the β- and α-isomers are mixed in the equivalent amount.

A measure for solving the above-noted problems inherent in the conventional methods is proposed in, for example, Japanese Patent Application No. 2-133913 and "Chem. Lett., 1990, page 1549". It is proposed that a condensation reaction is carried out between a 2,3-dideoxy-2-α-(organothio)pentofuranose derivative and a 5-substituted pyrimidine derivative in the presence of Lewis acid so as to obtain a 1-(2,3-dideoxy-2-organothio-β-D-pentofuranosyl) pyrimidine derivative. The derivative thus obtained is oxidized in the presence of a peroxide to obtain 2',3'-dideoxy-2',3'-didehydro-β-ribonucleoside via a 1-(2,3-dideoxy-2-organosulfynyl-β-D-pentofuranosyl) pyrimidine derivative.

It should be noted that an organothio group is α-coordinated with the carbon atom in 2-position of the 2,3-dideoxy-2-α-(organothio)pentofuranose derivative used as one of the starting materials in the method described above. Thus, in the condensation reaction between the pentofuranose derivative and the 5-substituted pyrimidine derivative, the approach of the 5-substituted pyrimidine derivative toward the organothio group in an α direction is inhibited by the steric effect of the organothio group and involvement of the adjacent group. As a result, a high selectivity of the β-isomer of the resultant pyrimidine derivative can be achieved. It follows that the method described above permits obtaining 2',3'-dideoxy-2',3'-didehydro-β-ribonucleoside in a high stereoselectivity.

As described above, the conventional method described above permits achieving a high selectivity of the β-isomer in the condensation reaction between the 2,3-dideoxy-2-α-(organothio)pentofuranose derivative and the 5-substituted pyrimidine derivative. However, it is difficult to obtain the α-isomer with a high stereoselectivity in the step of preparing the 2,3-dideoxy-2-α-(organothio)pentofuranose derivative, thus, the starting material, from a 5-hydroxypentan-4-olide derivative by the conventional method. As a result, the yield of the β-isomer is relatively low, i.e., about 30%, in the process ranging between the step of obtaining 2,3-dideoxy-2-α-(organothio)pentofuranose derivative from the 5-hydroxypentan-4-olide derivative and the step of the condensation reaction.

DISCLOSURE OF THE INVENTION

The present invention, which has been achieved in view of the situation described above, is intended to provide a method of manufacturing 2',3'-dideoxy-β-nucleoside derivatives with a high yield by a simple manufacturing process.

The present inventors have found that 2',3'-dideoxy-β-nucleoside derivatives can be obtained by the process comprising a condensation reaction between a 2,3-dideoxy-2,2-di(organothio)pentofuranose derivative, which is obtained by introducing two organothio groups into the carbon atom in 2-position of a 2,3-dideoxy-pentofuranose derivative, and a 5-substitued pyrimidine derivative, and, then, a reductive desulfurization reaction applied to the condensate thus obtained.

According to the present invention, there is provided a method of manufacturing a 2',3'-dideoxy-β-nucleoside derivative (I), comprising the steps of:

(a) preparing a 2,3-dideoxy-2,2-di(organothio)pentofuranose derivative (IV) from a 5-hydroxypentane-4-olide derivative (VI);

(b) carrying out a condensation reaction between the prepared 2,3-dideoxy-2,2-di(organothio)pentofuranose derivative (IV) and a 5-substituted pyrimidine derivative (V) to prepare a 1-[2,3-dideoxy-2,2-di(organothio)-β-D-pentofuranosyl]pyrimidine derivative (III);

(c) desulfurizing and reducing the 1-[2,3-dideoxy-2,2-di(organothio)-β-D-pentofuranosyl]pyrimidine derivative (III) prepared in step (b) to prepare a 1-

(2,3-dideoxy-β-D-pentofuranosyl)pyrimidine derivative (II); and (d) subjecting the 1-(2,3-dideoxy-β-D-pentofuranosyl)pyrimidine derivative (II) prepared in step (c) to a reaction for removing the protective group so as to obtain 2',3'-dideoxy-β-nucleoside derivative (I):

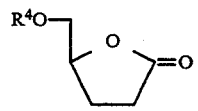
(VI)

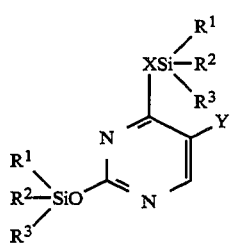
(V)

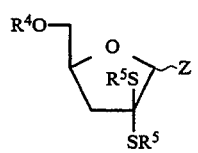
(IV)

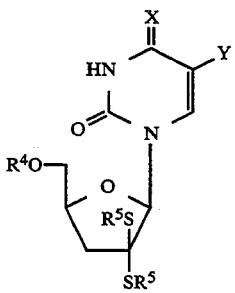
(III)

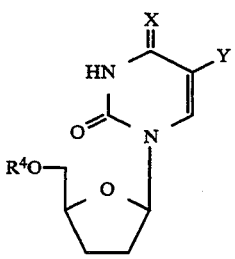
(II)

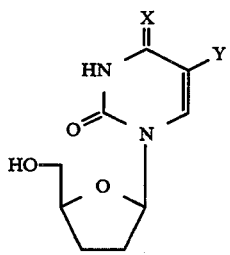
(I)

where R¹ to R⁵, X, Y and Z are represented as follows:
R¹ to R³, which may be the same or different, are alkyl or phenyl group, which may be substituted;
R⁴ is a protective group of a hydroxyl group;
R⁵ is alkyl or phenyl group, which may be substituted;

X is oxygen or nitrogen atom, said nitrogen atom having another atom or an atomic group;

Y is hydrogen atom, halogen atom, alkyl group or alkenyl group, said alkyl or alkenyl group being possibly substituted with a halogen atom; and Z is halogen atom, acyloxy, alkyloxy or aryloxy group, said alkyloxy and phenyloxy groups being possibly substituted.

The present invention also provides the intermediate compound (III) prepared in step (b) of the manufacturing method described above.

Particularly, preferred intermediate compound (III) includes three compounds described below.

First compound is represented by general formula given below:

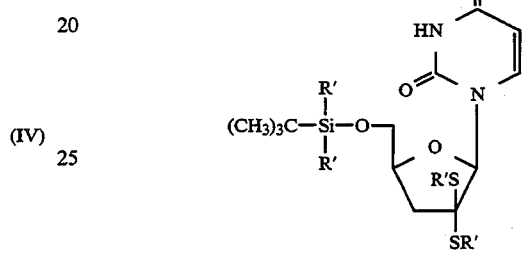

where R' is alkyl or phenyl group, which may be substituted.

Second compound is represented by general formula given below:

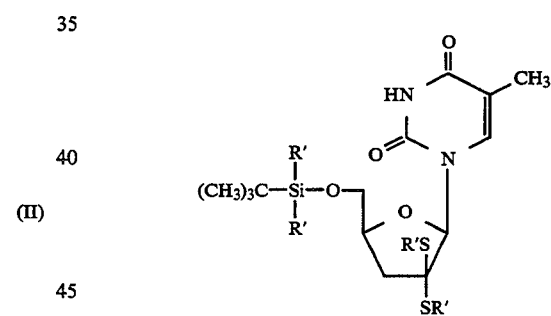

where R' is alkyl or phenyl group, which may be substituted.

Third compound is represented by general formula given below:

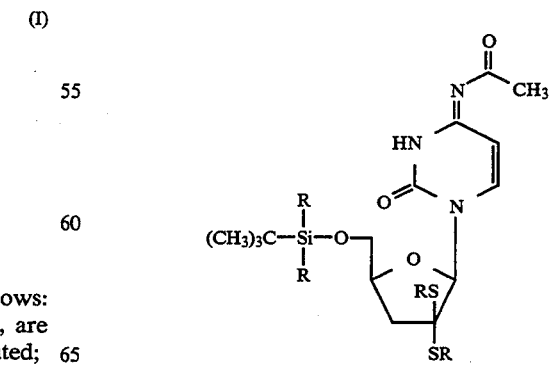

where R' is alkyl or phenyl group, which may be substituted.

Let us describe the manufacturing method of the present invention more in detail.

A 5-hydroxypentan-4-olide derivative (VI), which is one of the starting materials, can be obtained by the method described in, for example, Published Unexamined Japanese Patent Application No. 64-98 filed by Bristolmiyers Inc.

The $R^4$ used for protecting the hydroxyl group in 5-position of the 5-hydroxypentan-4-olide derivative (VI), as well as $R^4$ included in each of general formulas I and II, includes, for example, an aralkyl group such as benzyl and trityl; an acyl group such as acetyl, propionyl, pivaloyl, and benzoyl; an alkyoxycarbonyl group such as ethoxycarbonyl; aryloxycarbonyl group such as phenoxycarbonyl; and a triorganosilyl group such as trimethylsilyl, t-butyldimethylsilyl, and t-butyldiphenylsilyl. Where the protective group has a phenyl group, the phenyl group has a substituent such as alkyl group, halogen atom, nitro group, alkoxy group, etc., though the substituent is not particularly restricted. The protective group $R^4$ is introduced into 5-hydroxypentan-4-olide by an ordinary method.

The step (a) for obtaining the 2,3-dideoxy-2,2-di(organothio)pentofuranose derivative (IV) from the 5-hydroxypentan-4-olide derivative (VI) can be carried out by the ordinary method. For example, two organothio groups are introduced first into 2-position of the 5-hydroxypentan-4-olide derivative (VI) by employing, for example, the method of Trost et al. described in "J. Am. Chem. Soc, 1973, vol. 95, page 6840", or the method of Mukaiyama et al. described in "Bull. Chem. Soc. Japan, 1972, vol. 45, page 866. In the next step, the lactonecarbonyl group of the derivative (VI) is reduced by the method disclosed in, for example, Published Unexamined Japanese Patent Application No. 64-98, filed by Bristol-Myers Inc, referred to previously, followed by substituting the hydroxyl group in 1-position with the active group Z so as to obtain a 2,3-dideoxy-2,2-di(organothio)pentofuranose derivative (IV).

The group $SR^5$ used as an organothio group in 2-position of the 2,3-dideoxy-2,2-di(organothio)pentofuranose derivative (IV), or in formula II, denotes, for example, an alkylthio group such as methylthio or t-butylthio, an aralkylthio group such as benzylthio, and an arylthio group such as phenylthio. Where the organothio group $SR^5$ has a phenyl group, a substituent such as an alkyl group, a halogen atom, a nitro group or an alkoxy group may be substituted in the phenyl group. However, the organothio group $SR^5$ need not be restricted to those exemplified above.

The Z introduced as an active group in 1-position of 2,3-dideoxy-2,2-di(organothio)pentofuranose derivative (IV) includes, for example, a halogen atom such as fluorine, chlorine, or bromine; an alkyloxy group such as methoxy; an aryloxy group such as phenoxy; an acyloxy group such as acetyloxy, propionyloxy, pivaloyloxy or benzoyloxy; an alkyloxycarbonyloxy group such as ethoxycarbonyloxy; and an aryloxycarbonyloxy group such as phenoxycarbonyloxy. Where the Z has a phenyl group, a substituent such as an alkyl group, a halogen atom, a nitro group or an alkoxy group may be substituted in the phenyl group. However, the Z need not be restricted to those exemplified above.

As described above, two organothio groups are introduced into 2-position of the 2,3-dideoxy-2,2-di(organothio)pentofuranose derivative (IV). Thus, stereoisomers of the derivative (IV) are not formed, making it possible to obtain a pure compound.

On the other hand, the 5-substituted pyrimidine derivative (V) used in step (b) can be obtained by silylating the carbonyl group in 2-position and the X in 4-position of the pyrimidine so as to introduce a triorganosilyl group. The silylation of the 5-substituted pyrimidine derivative (V) can be carried out by, for example, the method of Forbriggen et al. described in "Chem. Ber., 1981, vol. 114, page 1234". Specifically, the silylation can be achieved by adding trimethylsilylchloride to a hexamethyldisilazane suspension of the pyrimidine, followed by heating the resultant suspension for reflux under an argon gas atmosphere. However, the silylating method need not be restricted to that exemplified above.

The pyrimidine used in the present invention includes thymine, uracil, cytosine, which can be obtained by decomposing nucleic acid present in the nature, pyrimidine synthesized from these natural bases by the ordinary method, and other synthetic pyrimidine which are not derived from natural substances and are completely synthesized.

The triorganosilyl group introduced by the silylating reaction into the 5-substituted pyrimidine derivative (V) is equal to the ordinary protective group of hydroxyl group or amino group and includes, for example, trimethylsilyl, t-butyldimethylsilyl and phenydimethylsilyl groups. However, the triorganosilyl group is not restricted to those exemplified above.

The X included in general formula V represents an oxygen atom or a nitrogen atom. The nitrogen atom is bonded to an atom or an atomic group such as a hydrogen atom, an alkyl group or an acyl group.

The Y included in general formula V represents a hydrogen atom; a halogen atom such as a fluorine atom, a chlorine atom, a bromine atom or a iodine atom; and an alkyl or alkenyl group which may be substituted by a halogen atom.

A condensation reaction is carried out in step (b) between the 2,3-dideoxy-2,2-di(organothio)pentofuranose derivative (IV) and the 5-substituted pyrimidine derivative (V) as following. Thus, the amount of the 5-substituted pyrimidine derivative (V) should be at least equal to that of the pentofuranose derivative (IV) in terms of the equivalent weight. Preferably, 2 equivalents of the derivative (V) should be used relative to 1 equivalent of the derivative (IV), and the condensation reaction should be carried out in the presence of a Lewis acid. The Lewis acid used in the present invention includes, for example, trimethylsilyl trifluoromethane sulfonate, tin tetrachloride and titanium tetrachloride. The condensation reaction should be carried out under, for example, an ambient temperature within an aprotic solvent, e.g., methylene chloride, 1,2-dichloroethane, or acetonitrile, in the presence of a Lewis acid in an amount effective for the catalytic function, e.g., in an amount falling within a range between 20 mol % and 2.5 equivalents. In general, the condensation reaction is completed in 1 to 5 hours. After the condensation reaction, the reaction mixture is subjected to after-treatments, as required, such as treatment with an aqueous solution of sodium hydrogencarbonate and extraction with an organic solvent. Then, the $\beta$-isomer is purified and isolated by a known method such as chromatography so as to obtain 1-[2,3-dideoxy-2,2-di(organothio)-$\beta$-D-pentofuranosyl]pyrimidine derivative (III).

The desulfurizing reducing reaction of the pyrimidine derivative (III) is carried out in step (c) in the presence of a hydrogenated organic tin compound. A compound generally used in a reductive desulfurization of a sulfide, for example, hydrogenated tributyl tin or hydrogenated triphenyl tin, can be used as the hydrogenated organic tin compound. The reducing reaction should be carried out under temperatures falling within a range of ambient temperature to about 150° C., preferably 80° C. to 100° C. within a suitable solvent, particularly a hydrocarbon solvent such as benzene or toluene. The amount of the hydrogenated organic tin compound should be at least equal to that of the pyrimidine derivative (III) in terms of the equivalent weight, for example, 5 equivalents relative to 1 equivalent of the pyrimidine derivative (III). The reducing reaction can also be carried out under a condition that a hydrogenated tin compound is generated within the reaction solution, e.g., in the presence of both hexabutylditinoxide and polymethylsiloxane.

The reaction mixture obtained by the reducing reaction described above is subjected to separation by, for example, chromatography to obtain a pure compound of 1-(2,3-dideoxy-$\beta$-D-pentofuranosyl)pyrimidine derivative (II).

The elimination of the protective group from the pyrimidine derivative (II) in step (d) can be achieved by a known method, though the specific reaction for eliminations of the protective group differs depending on the kind of the protective group. For example, where the protective group is a triorganosilyl group, the protective group can be eliminated within a mixture of tetra(n-butyl)ammonium fluoride and anhydrous tetrahydrofuran. Where the protective group is an aralkyl group, the benzyl group can be eliminated by reduction under a hydrogen gas atmosphere in the presence of a hydrogenation catalyst. Where the protective group is a trityl group, the protective group can be eliminated by treatment within acetic acid.

Where the protective group is an acyl group, the protective group can be eliminated by, for example, an alkali hydrolysis, alcoholysis, or ammonolysis.

Where the protective group is an aryloxycarbonyl group or an alkyloxycarbonyl group, the protective group can be eliminated according to the same method as the acyl group.

The reaction mixture obtained by the reaction for eliminating the protective group is separated by means of crystallization or chromatography to obtain a desired pure compound of 2'-3'-dideoxy-$\beta$-ribonucleoside derivative (I).

In the method of the present invention for manufacturing 2'-3'-dideoxy-$\beta$-ribonucleoside, stereoisomers are not formed in the process of preparing 2,3-dideoxy-2,2-di(organothio)pentofuranose derivative (IV), which is one of the starting materials, as described previously, making the purification easy. As a result, the yield of $\beta$-isomer in the process ranging between the step of obtaining 2,3-dideoxy-2-2-di(organothio)pentofuranose derivative (IV) from the 5-hydroxypentan-4-olide derivative (VI) and the step of the condensation reaction is about 35%. Also, the yield of the final product, i.e., 2',3'-dideoxy-$\beta$-ribonucleoside, throughout the entire process is about 20%.

As described above, the method of the present invention makes it possible to synthesize easily 2',3'-dideoxy-$\beta$-nucleoside, which is very useful in industries, and permits supplying the compound stably in a large amount.

BEST MODE OF EMBODYING THE INVENTION

Let us describe the present invention more in detail with reference to Examples which follow.

EXAMPLE 1

(Manufacture of 2',3'-dideoxy-$\beta$-uridine)

Step (1) Manufacture of 5-(t-butyldiphenylsilyloxy)-2,2-di(phenylthio)pentan-4-olide:

To a suspension prepared by suspending 0.363 g (1.02 mmol) of 5-(t-butyldiphenylsilyloxy)pentan-4-olide and 0.570 g (2.23 mmol) of N-phenylthiophthalimide in 3 ml of anhydrous tetrahydrofuran, 2.3 ml (2.3 mmol) of tetrahydrofuran solution containing of lithium bis(-trimethylsilyl)amide whose amount is 1.0 mol per liter of that of the solution was added dropwise under an argon gas atmosphere at $-78°$ C. After completion of the adding dropwise, the reaction solution was slowly heated to room temperature, followed by stirring the solution for 1.5 hours. After completion of the reaction, the reaction solution was poured into a saturated aqueous solution of ammonia sulfate, followed by extraction with diethyl ether. The organic layer was dried with anhydrous magnesium sulfate, followed by removing the solvent by distillation under a reduced pressure so as to obtain a residue.

The residue was purified by means of a silica gel column chromatography (n-hexane: ethyl acetate=10:1) so as to obtain 0.438 g (0.766 mol) of 5-(t-butyldiphenylsilyloxy)-2,2-di(phenylthio)pentan-4-olide (yield of 75%).

The physical data of the product thus obtained were as follows: $^1$H-NMR (CDCl$_3$): $\delta$ 7.69–7.56 (8H, m, aromatic H), 7.48–7.25 (12H, m, aromatic H), 4.50–4.39 (1H, m, H-4), 3.71 (1H, dd, J=11.7, 3.6 Hz, H-5), 3.54 (1H, dd, J=11.6, 4.3 Hz, H-5), 2.63 (1H, dd, J=14.0, 9.5 Hz, H-3), 2.21 (1H, dd, J=14.0, 6.0 Hz, H-3), 0.98 (9H, s, t-Bu)

Step (2) Manufacture of 1-O-acetyl-5-O-(t-butyl diphenylsilyl)-2,3-dideoxy-2,2-di(phenylthio)-D-glyceropentofuranose:

To a solution prepared by dissolving 4.00 g (7.00 mmol) of 5-(t-butyldiphenylsilyloxy)-2,2-di(phenylthio)pentan-4-olide obtained in step (1) in 45 ml of anhydrous tetrahydrofuran, 15 ml (15 mmol) of toluene solution containing hydrogenated di(i-butyl)aluminum whose amount is 1 mol per liter of that of the solution was added dropwise under an argon gas atmosphere at 0° C. After the adding dropwise, the resultant solution was stirred for 1.5 hours as it is. After the reaction, a small amount of water was added to the reaction solution. Then, the reaction solution was heated to room temperature, followed by adding anhydrous magnesium sulfate. A solid material generated was removed by filtration using Celite, followed by removing the solvent in the solution by distillation under a reduced pressure so as to obtain a residue.

The residue thus obtained was purified by means of a silica gel column chromatography (n-hexane:ethyl acetate=6:1) so as to obtain 5-O-(t-butyldiphenylsilyl)-2,3-dideoxy-2,2-di(phenylthio)-D-glycero-pentofuranose.

The compound thus obtained was dissolved in 30 ml of anhydrous dichroromethane, followed by adding 1 ml (10.6 mmol) of acetic anhydride and 50 mg of 4-(N,N-dimethylamino)pyridine. The resultant solution was stirred overnight in the absence of water. After completion of the reaction, the reaction solution was poured into a saturated aqueous solution of sodium hydrogencarbonate, followed by extraction with chloroform. The organic layer was dried with anhydrous magnesium sulfate, followed by removing the solvent by distillation under a reduced pressure so as to obtain a residue.

The residue thus obtained was refined with a silica gel column chromatography (n-hexane:ethyl acetate=85:15) so as to obtain 3.17 g (5.14 mmol) of 1-O-acetyl-5-O-(t-butyldiphenylsilyl)-2,3-dideoxy-2,2-di(-phenylthio)-D-glycero-pentofuranose (yield; 73%).

The physical data of the product thus obtained were follows: $^1$H-NMR (CDCl$_3$): δ 7.73–7.53 (8H, m, aromatic H), 7.45–7.30 (12H, m, aromatic H), 6.40 (0.4H, s, H-1 minor), 6.20 (0.6H, s, H-1 major), 4.55–4.41 (1H, m, H-4), 3.77–3.64 (2H, m, H-5), 2.42 (0.6H, dd, J=13.4, 9.6 Hz, H-3 major), 2.29 (0.4H, dd, J=14.5, 6.9 Hz, H-3 minor), 2.21 (0.4H, dd, J=14.5, 7.6 Hz, H-3 minor), 2.07–2.01 (1.8H, m, H-3 major, Ac minor), 1.88 (1.8H, s, Ac major), 1.00 (9H, s, t-Bu)

Step (3) Manufacture of 1-[5-O-(t-butyldiphenylsilyl)-2,3-dideoxy-2,2-di(phenylthio)-D-glyceropentofuranosyl]uracil:

0.1 ml of tetramethylsilylchloride was added to a suspension prepared by suspending 0.610 g (5.43 mmol) of uracil in 10 ml of hexamethyldisilazane, followed by subjecting the resultant solution to reflux under heating for 30 minutes under an argon gas atmosphere. When the suspended crystals were completely dissolved, the solution was cooled to room temperature. Thereafter, the substance having a low boiling point was removed by distillation under a reduced pressure achieved by using a vacuum pump so as to obtain an oily residue.

Added to the residue thus obtained was a solution prepared by dissolving 2.23 g (3.62 mmol) of 1-O-acetyl-5-O-(t-butyldiphenylsilyl)-2,3-dideoxy-2,2-di(phenylthio)-D-glycero-pentofuranose obtained in step (2) in 20 ml of anhydrous 1,2-dichloroethane. Further, 2 ml of anhydrous 1,2-dichloroethane solution containing 0.10 ml (0.5 mmol) per milliliter of triethylsilyl trifluoromethane sulfonate was slowly added to the resultant solution under an argon gas atmosphere, followed by being stirred the reaction solution thus prepared for 4 hours at room temperature. After completion of the reaction, the reaction solution was poured into a saturated aqueous solution of sodium hydrogencarbonate, followed by extraction with chloroform. The organic layer was dried with anhydrous magnesium sulfate, followed by removing the solvent by distillation under a reduced pressure.

The residue thus obtained was purified with a silica gel column chromatography (n-hexane:ethyl acetate=3:2). 1.89 g of a refined product thus obtained was found to be a mixture of 1-[5-O-(t-butyldiphenylsilyl)-2,3-dideoxy-2,2-di(phenylthio)-β-D-glycero-pentofuranosyl]uracil(β-isomer) and α-isomer thereof. The mixing ratio was found to be β:α=76:24 (yield of 78%). Further, the yield of the β-isomer throughout the process from the starting material of 5-(t-butyldiphenylsilyloxy)pentan-4-olide to the β-isomer was found to be 35%.

The mixture was separated into its isomers by means of a high performance liquid chromatography (fixed phase; se: A-363, manufactured by YMC Inc., ODS, 30 mm in diameter×250 mm in length; moving phase; acetonitrile:water=85:15, flowing rate of 10 ml/min; detection:ultraviolet absorption, λ=254 nm).

The physical data of the product were as follows: 1-[5-O-(t-butyldiphenylsilyl)-2,3-dideoxy-2,2-di(phenylthio)-β-D-glycero-pentofuranosyl]uracil.

Angle of rotation: [α]$_D$−8.4° (c 1.03, CHCl$_3$, 24° C.) $^1$H-NMR (CDCl$_3$): δ 8.03–7.96 (2H, m, H-6, NH), 7.82–7.77 (2H, m, aromatic H), 7.58–7.25 (18H, m, aromatic H), 6.35 (1H, s, H-1'), 5.26 (1H, dd, J=8.2, 1.9 Hz, H-5), 4.53–4.45 (1H, m, H-4'), 4.14 (1H, dd, J=12.2, 2.0 Hz, H-5') 3.62 (1H, dd, J=12.2, 2.1 Hz, H-5') 2.53 (1H, dd, J=13.8, 11.1 Hz, H-3') 1.82 (1H, dd, J=13.7, 4.8 Hz, H-3') 1.03 (9H, s, t-Bu) $^{13}$C-NMR (CDCl$_3$): δ 162.62 (C-4), 149.89 (C-2), 140.82 (C-6), 137.20 (aromatic C), 135.52 (aromatic C), 135.33 (aromatic C), 132.53 (aromatic C), 132.03 (aromatic C), 131.01 (aromatic C), 130.15 (aromatic C), 130.09 (aromatic C), 130.01 (aromatic C), 129.40 (aromatic C), 129.05 (aromatic C), 129.01 (aromatic C), 127.95 (aromatic C), 101.76 (C-5), 90.37 (C-1'), 80.15 (C-4'), 72.96 (C-2'), 62.85 (C-5'), 38.87 (C-3'), 26.89 (t-Bu), 19.28 (t-Bu) IR (KBr): ν(cm$^{-1}$) 1690(s), 1265(m), 1114(m), 748(m), 702(m), 505(m) MS(EI-DI): m/z 610(M$^+$—C$_4$H$_8$), 558 (M$^+$+H—C$_6$H$_5$S) UV (CHCl$_3$): λ$_{max}$ 265 nm (log ε 4.11)

1-[5-O-(t-butyldiphenylsilyl)-2,3-dideoxy-2,2-di(-phenylthio)-α-D-glycero-pentofuranosyl]uracil.

Angle of rotation: [α]$_D$−69.0° (c 1.00, CHCl$_3$, 25° C.) $^1$H-NMR (CDCl$_3$): δ 9.78 (1H, d, J=1.9 Hz, NH), 7.85–7.65 (5H, m, H-6, aromatic H), 7.58–7.52 (4H, aromatic H), 7.47–7.28 (12H, m, aromatic H), 6.43 (1H, s, H-1'), 5.75 (1H, dd, J=8.2, 2.2 Hz, H-5), 4.52–4.44 (1H, m, H-4'), 3.67 (1H,dd, J=11.4, 3.7 Hz, H-5'), 3.51 (1H, dd, J=11.4, 4.0 Hz, H-5'), 2.27 (1H, dd, J=13.9, 9.9 Hz, H-3'), 1.91 (1H, dd, J=13.8, 5.2 Hz, H-3'), 0.91 (9H, s, t-Bu) $^{13}$C-NMR (CDCl$_3$): δ 163.44 (C-4), 150.89 (C-2), 141.10 (C-6), 137.45 (aromatic C), 135.88 (aromatic C), 135.52 (aromatic C), 135.45 (aromatic C), 133.04 (aromatic C), 132.83 (aromatic C), 130.39 (aromatic C), 129.94 (aromatic C), 129.71 (aromatic C), 129.65 (aromatic C), 129.10 (aromatic C), 128.99 (aromatic C), 127.63 (aromatic C), 101.03 (C-5), 89.79 (C-1'), 78.21 (C-4'), 69.52 (C-2'), 64.49 (c-5'), 38.05 (C-3'), 26.69 (t-Bu), 19.03 (t-Bu) IR (KBr): ν (cm$^{-1}$) 1694 (s), 1265 (m), 1112 (m), 1085 (m), 748 (m), 505 (m) MS (EI-DI): m/z 610 (M$^+$-C$_4$H$_8$), 558 (M$^+$+H—C$_6$H$_5$S) UV (CHCl$_3$): λ$_{max}$ 264 nm (log ε 4.18)

Step (4) Manufacture of 1-[5-O-(t-butyldiphenylsilyl)-2,3-dideoxy-β-D-glycero-pentofuranosyl]uracil:

To a solution prepared by dissolving 7 mg (0.10 mmol) of 1-[5-O-(t-butyldiphenylsilyl)-2,3-dideoxy-2,2-di(phenylthio)-β-D-glycero-pentofuranosyl]uracil prepared in step (3) in 10 ml of anhydrous benzene, 150 μl (0.57 mmol) of hydrogenated tributyl tin and 10 mg of azobisisobutylonitrile were added, followed by subjecting the resultant solution to a reflux under heating for 48 hours under an argon gas atmosphere. After completion of the reaction, a low boiling point substances were removed by distillation under a reduced pressure so as to obtain a residue.

The residue thus obtained was purified by means of a thin layer classifying chromatography (silica gel; n-hexane:ethyl acetate=1:1) so as to obtain 25 mg of 1-[5-O-(t-butyldiphenylsilyl)-2,3-dideoxy-β-D-glycero-pentofuranosyl]uracil (yield of 56%).

The physical data of the product were as follows:
¹H-NMR (CDCl₃): δ 8.87 (1H, br, NH), 7.99 (1H, J=8.1 Hz, H-6), 7.70–7.62 (4H, m, aromatic H), 7.48–7.36 (6H, m, aromatic H), 6.11 (1H, dd, J=6.6, 2.8 Hz, H-1'), 5.41 (1H, dd, J=8.1, 2.1 Hz, H-5), 4.17–4.09 (2H, m, H-4', H-5'), 3.73 (1H, dd, J=11.5, 2.6 Hz, H-5'), 2.51–2.35 (1H, m, H-2') 2.18–2.04 (2H, m, H-2', H-3'), 1.98–1.88 (1H, m, H-3'), 1.09 (9H, s, t-Bu)

Step (5) Manufacture of 2',3'-dideoxy-β-uridine:

2.5 ml (2.5 mmol) of tetrahydrofuran solution containing 1.0 mol per liter of tetra(n-butyl)ammonium fluoride was added to a solution prepared by dissolving 897 mg (2.0 mmol) of 1-[5-O-(t-butyldiphenylsilyl)-2,3-dideoxy-β-D-glycero-pentofuranosyl]uracil prepared in step (4) in 10 ml of anhydrous tetrahydrofuran, followed by stirring the resultant solution at room temperature for 80 minutes in the absence of water. After completion of the reaction, the solvent was removed by distillation under a reduced pressure so as to obtain a residue.

The residue thus obtained was purified by means of silica gel chromatography (chloroform: methanol=91:9) so as to obtain 394 mg (1.9 mm) of 2',3'-dideoxy-β-uridine (yield of 95%).

The yield of 2',3'-dideoxy-β-uridine was about 20%, which was obtained from the starting material of 5-(t-butyldiphenylsilyloxy)pentan-4-olide throughout the steps (1) to (5).

EXAMPLE 2

Manufacture of 2',3'-dideoxy-thymidine

Step (3b) Manufacture of 1-[5-O-(t-butyldiphenylsilyl)-2,3-dideoxy-2,2-di(phenylthio)-D-glycero-pentofuranosyl]thymide:

6 ml of hexamethyldisilazane and 4.5 ml of trimethyl silyl chloride were added to a suspension prepared by suspending 0.660 g (5.22 mmol) of thymine in 30 ml of 1,2-dichloroethane, followed by subjecting the resultant suspension to a reflux under heating for 3 hours under an argon gas atmosphere, when the suspended crystals were completely dissolved, the suspension was cooled to room temperature. After the cooling, low boiling point substances were removed by distillation under a reduced pressure achieved by using a vacuum pump so as to obtain an oily residue.

Added to the residue thus obtained was a solution prepared by dissolving 1.61 g (2.61 mmol) of 1-O-acetyl-5-O-(t-butyldiphenylsilyl)-2,3-dideoxy-2,2-di(phenylthio)-D-glycero-pentofuranose, which was obtained according to same method as the step (2) in Example 1, in 14 ml of anhydrous acetonitrile. Also added slowly at 0° C. under an argon gas atmosphere was 2 ml of an anhydrous acetonitrile solution containing 0.26 ml (1.3 mmol) of trimethylsilyl trifluoromethane sulfonate. The resultant solution was stirred as it was for 3 hours. After completion of the reaction, the reaction solution was poured into a saturated aqueous solution of sodium hydrogencarbonate, followed by extraction with chloroform. The organic layer was dried with anhydrous magnesium sulfate, followed by removing the solvent by distillation under a reduced pressure so as to obtain a residue.

The residue thus obtained was purified by silica gel column chromatography (n-hexane: ethyl acetate=3:2). 1.07 g of a purified material was found to be a mixture of the desired product of 1-[5-O-(t-butyldiphenylsilyl)-2,3-dideoxy-2,2-di(phenylthio)-β-D-glycero-pentofuranosyl] thymine and an α-isomer thereof. The mixing ratio was β:α=81:19 (yield of 60%).

The purified material was separated into its isomers by means of a high performance liquid chromatography (fixed phase: A-363, ODS manufactured by YMC Inc., 30 mm in diameter×250 mm in length; moving phase; acetonitrile:water=85:15, flowing rate of 15 ml/min; detection:ultraviolet absorption, λ=254 nm).

The physical data of the product were as follows: 1-[5-O-(t-butyldiphenylsilyl)-2,3-dideoxy-2,2-di(phenylthio)-β-D-glycero-pentofuranosyl]thymine.

Angle of rotation: $[\alpha]_D$ 18.7° (cl. 01, CHCl₃, 25° C.)
¹H-NMR (CDCl₃): δ 8.44 (1H, br, NH), 7.79–7.74 (2H, m, aromatic H), 7.66–7.55 (4H, m, aromatic H), 7.52–7.23 (15H, m, aromatic H, H-6), 6.41 (1H, s, H-1'), 4.43–4.34 (1H, m, H-4'), 4.06 (1H, dd, J=11.9, 2.6 Hz, H-5'), 3.72 (1H, dd, J=11.9, 3.3 Hz, H-5'), 2.40 (1H, dd, J=13.6, 10.8 Hz, H-3'), 1.97 (1H, dd, J=13.6, 4.8 Hz, H-3'), 1.57 (3H, s, Me), 1.06 (9H, s, t-Bu) ¹³C-NMR (CDCl₃): δ 163.44 (C-4), 150.05 (C-2), 137.12 (aromatic C), 136.30 (C-6), 135.45 (aromatic C), 135.28 (aromatic C), 134.33 (aromatic C), 132.98 (aromatic C), 132.57 (aromatic C), 131.42 (aromatic C), 130.35 (aromatic C), 130.05 (aromatic C), 130.00 (aromatic C), 129.94 (aromatic C), 129.02 (aromatic C), 128.83 (aromatic C), 127.84 (aromatic C), 109.95 (C-5), 90.48 (C-1'), 79.17 (C-4'), 72.32 (C-2'), 63.40 (C-5'), 40.20 (C-3'), 26.97 (t-Bu), 19.39 (t-Bu), 12.03 (Me) IR (KBr): ν (cm⁻¹) 1690 (s), 1473 (m), 1263 (m), 1114 (m), 1077 (m), 754 (m), 702 (m), 505 (m) MS (EI-Di): m/z 624 (M⁺—C₄H₈), 572 (M⁺+H—C₆H₅s) UV (CHCl₃): $\lambda_{max}$ 266 nm (log ε 4.13) 1-[5-O-(t-butyldiphenylsilyl)-2,3-dideoxy-2,2-di(-phenylthio)-α-D-glycero-pentofuranosyl]thymine.

Angle of rotation: $[\alpha]_D$ —57.7° (co. 50, CHCl₃, 25° C.)
¹H-NMR (CDCl₃): δ 9.46 (1H, br, NH), 7.82–7.76 (2H, ml aromatic H), 7.70–7.66 (2H, M, aromatic H), 7.58–7.52 (5H, m, aromatic H, H-6), 7.47–7.29 (12H, m, aromatic H), 6.45 (1H, s, H-1'), 4.56–4.46 (1H, m, H-4'), 3.69 (1H, dd J=11.3. 3.8 Hz, H-5'), 3.54 (1H, dd, J=11.3, 3.9 Hz, H-5'), 2.30 (1H, dd, J=13.9, 9.8 Hz, H-3'), 2.00–1.89 (4H, m, H-3', Me), 0.93 (9H, s, t-Bu), ¹³C-NMR (CDCl₃): δ 163.84 (C-4), 150.93 (C-2), 137.37 (aromatic C), 136.71 (C-6), 135.52 (aromatic C), 135.45 (aromatic C), 133.05 (aromatic C), 132.82 (aromatic C), 130.45 (aromatic C), 130.18 (aromatic C), 129.88 (aromatic C), 129.71 (aromatic C), 129.43 (aromatic C), 129.06 (aromatic C), 128.87 (aromatic C), 127.63 (aromatic C), 109.17 (C-5), 89.73 (C-1'), 78.10 (C-4'), 69.59 (C-2'), 64.55 (C-5'), 38.53 (C-3'), 26.70 (t-Bu), 19.05 (t-Bu), 12.71 (Me) IR (KBr): ν (cm⁻¹) 1692 (s), 1473 (m), 1265 (m), 1114 (m), 1085 (m), 745 (m), 704 (m), 505 (m) MS (EI-DI): m/z 610 (M⁺—C₄H₈), 572 (M⁺+H—C₆H₅s) UV (CHCl₃): $\lambda_{max}$ 267 nm (log ε 4.14)

Step (4b) Manufacture of 1-[5-O-(t-butyldiphenylsilyl)-2,3-dideoxy-β-D-glycero-pentofuranosyl]thymine:

150 μl (0.57 mmol) of hydrogenated tributyl tin and 10 mg of azobisisobutylonitrile were added to a solution prepared by dissolving 68 mg (0.10 mmol) of 1-[5-O-(t-butyldiphenylsilyl)-2,3-dideoxy-2,2-di(phenylthio)-β-D-glycero-pentofuranosyl]thymine obtained in step 3b, followed by subjecting the resultant solution to a reflux under heating for 48 hours under an argon gas atmosphere. After completion of the reaction, low boiling point substances were removed by distillation under a reduced pressure so as to obtain a residue.

The residue thus obtained was purified by a preparative thin layer chromatography (silica gel; n-hexane:ethyl acetate=1:1) so as to obtain 30 mg of 1-[5-O-(t-butyldiphenylsilyl)-2,3-dideoxy-β-D-glycero-pentofuranosyl]thymine (yield of 64%).

The physical data of the product were as follows:
1H-NMR (CDCl3): δ 8.83 (1H, br, NH), 7.71–7.65 (4H, m, aromatic H), 7.48–7.35 (7H, m, aromatic H, H-6), 6.12 (1H, dd, J=6.3, 4.7 Hz, H-1'), 4.20–4.17 (1H, m, H-4'), 4.03 (1H, dd, J=11.4, 2.8 Hz, H-5'), 3.75 (1H, dd, J=11.4, 3.4 Hz, H-5'), 2.46–2.34 (1H, m, H-2'), 2.12–1.94 (3H, m, H-2', H-3'), 1.64 (3H, d, J=1.2 Hz, Me), 1.10 (9H, s, t-Bu)

Step (5b) Manufacture of 2',3'-dideoxy-β-thymidine:

2.5 ml (2.5 mmol) of a tetrahydrofuran solution containing 1 mol per liter of tetra (n-butyl)ammonium fluoride was added to a solution prepared by dissolving 925 mg (2.0 mmol) of 1-[5-O-(t-butyldiphenylsilyl)-2,3-dideoxy-β-D-glycero-pentofuranosyl]thymine obtained in the step (4b) in 10 ml of anhydrous tetrahydrofuran, followed by stirring the resultant solution at room temperature for 70 minutes in the absence of water. After completion of the reaction, the solvent was removed by distillation under a reduced pressure so as to obtain a residue.

The residue thus obtained was purified by silica gel column chromatography (chloroform:methanol=91:9) so as to obtain 440 mg (2.0 mmol) of 2',3'-dideoxy-β-thymidine (yield of 100%).

The yield of the 2',3'-dideoxy-β-thymidine was 16%, which was finally obtained from the starting material of 5-(t-butyldiphenylsilyloxy)pentan-4-olide.

We claim:
1. A compound represented by formula (III)

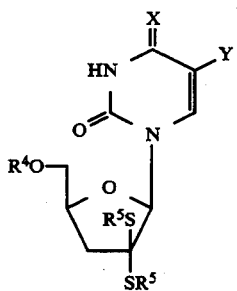

(III)

wherein $R^4$ is a hydroxyl protecting group;
$R^5$ is alkyl, aralkyl or aryl group, wherein aralkyl or aryl is a phenyl group or a phenyl group substituted with a moiety selected from the group consisting of halogen, nitro, and alkoxy;
X is oxygen or nitrogen, said nitrogen being bonded to a hydrogen, an alkyl group or an acyl group; and
Y is hydrogen, halogen, alkyl, or alkenyl, wherein said alkyl and alkenyl have substituents selected from the group consisting of hydrogen and halogen.

2. The compound according to claim 1, said compound being represented by

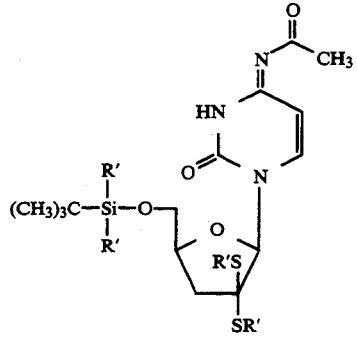

wherein R' is alkyl, aralkyl or aryl group, wherein said aralkyl and aryl group is phenyl or a phenyl substituted with a moiety selected from the group consisting of halogen, nitro, and alkoxy.

3. The compound according to claim 1, said compound being represented by wherein R' is alkyl, aralkyl or aryl group, wherein said aralkyl and aryl group is phenyl or a phenyl substituted with a moiety selected from the group consisting of halogen, nitro, and alkoxy.

4. The compound according to claim 1, said compound being represented by:

wherein R' is alkyl, aralkyl or aryl group, wherein said aralkyl and aryl group is phenyl or a phenyl substituted with a moiety selected from the group consisting of halogen, nitro, and alkoxy.

* * * * *